United States Patent [19]

Kirk et al.

[11] E Patent Number: Re. 33,574

[45] Reissued Date of Patent: Apr. 23, 1991

[54] SUBSTITUTED BIPHENYL DERIVATIVES

[75] Inventors: Alan R. Kirk, Cottage Grove; Robert A. Scherrer, White Bear Lake, both of Minn.

[73] Assignee: Riker Laboratories, Inc., St. Paul, Minn.

[21] Appl. No.: 469,204

[22] Filed: Jan. 24, 1990

Related U.S. Patent Documents

Reissue of:

[64] Patent No.: 4,710,515
Issued: Dec. 1, 1987
Appl. No.: 26,877
Filed: Mar. 17, 1987

[51] Int. Cl.[5] ..... A61K 31/195

[52] U.S. Cl. ..... 514/563; 514/562; 514/535; 562/455; 562/432; 562/426; 560/16; 560/43

[58] Field of Search ..... 562/455, 432, 426; 560/16, 43; 514/563, 562, 535

[56] References Cited

U.S. PATENT DOCUMENTS

| | | | |
|---|---|---|---|
| 4,055,653 | 10/1977 | Offermanns et al. | 514/563 |
| 4,067,895 | 1/1978 | Hofer et al. | 562/455 |
| 4,094,857 | 6/1978 | Wolfe | 562/455 |
| 4,153,728 | 5/1979 | Wolff | 514/563 |
| 4,172,151 | 10/1979 | Moore | 514/647 |

OTHER PUBLICATIONS

Bailey et al., Ann. Rpts. Med. Chem., vol. 17, pp. 203–207 (1982).

Samuelsson, Science, vol. 220, pp. 568–575 (1983).

*Primary Examiner*—James H. Reamer

*Attorney, Agent, or Firm*—Gary L. Griswold; Walter N. Kirn; Robert W. Sprague

[57] ABSTRACT

Novel compounds which are 2,6-di-tertiary-butylphenols substituted in the 4 position by an acylaminophenyl group, which acylaminophenyl group is substituted by a moiety which includes a carboxyl group, are useful as inhibitors of leukotriene biosynthesis and as antiallergic agents.

13 Claims, No Drawings

SUBSTITUTED BIPHENYL DERIVATIVES

Matter enclosed in heavy brackets [ ] appears in the original patent but forms no part of this reissue specification; matter printed in italics indicates the additions made by reissue.

TECHNICAL FIELD

This invention relates to [novel] di-tertiary butyl phenols. *In another aspect, this invention relates to compounds* which exhibit antiallergic activity. [Pharmaceutical] *In yet another aspect, this invention relates to pharmaceutical* compositions containing such compounds and pharmacological methods of using such compounds [are also described].

BACKGROUND OF THE INVENTION

The leukotrienes are a novel group of biologically active mediators derived from arachidonic acid through the action of lipoxygenase enzyme systems. The leukotrienes are potent smooth muscle contracting agents, particularly on respiratory smooth muscle but also on other tissues. In addition, they promote mucous production, modulate vascular permeability changes and are potent inflammatory mediators in human skin. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The most important compound in the second group of leukotrienes, namely dihydroxy fatty acids, is Leukotriene $B_4$. This compound is a potent chemotactic agent for neutrophils and eosinophils, and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene $B_4$ is also a potent hyperalgesic agent, and can modulate vascular permeability changes through a neutrophil dependent mechanism. Both groups of leukotrienes are formed following oxygenation of arachidonic acid through the action of a lipoxygenase enzyme. See, for example, D. M. Bailey et al., Ann. Rpts. Med. Chem., 17, 203 (1982).

Respiratory Conditions

Asthma. The leukotrienes are potent spasmogens of human trachea, bronchus and lung parenchymal strips, and when administered to normal volunteers as aerosols, are 3,800 times more potent than histamine at including a 50% decrease in air flow at 30% of vital capacity. They mediate increases in vascular permeability in animals and promote mucous production in human bronchial explants. In addition, Leukotriene $B_4$ may also mediate mucous production, and could be an important mediator of neutrophil and eosinophil accumulation in asthmatic lungs. Lipoxygenase products are also thought to be regulators of mast cell degranulation, and recent studies with human lung mast cells have suggested that lipoxygenase inhibitors, but not corticosteroids, may suppress antigen-induced mast cell degranulation. In vitro studies have shown that antigen challenge of human lung results in the release of leukotrienes, and, in addition, purified human mast cells can produce substantial amounts of leukotrienes. There is, therefore, good evidence that the leukotrienes are important mediators of human asthma. Lipoxygenase inhibitors would, therefore, be a new class of drugs for the treatment of asthma. See, for example, B. Samuelsson, Science, 220, 568–575 (1983).

Psoriasis. Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured, as well as large amounts of lipoxygenase products. Leukotriene $B_4$ has been detected in psoriatic lesions, but not uninvolved skin, in biologically significant amounts.

Allergic Conditions

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis, gall bladder spasm and ulcerative colitis. In addition, they may have a role in cardiovascular disease because Leukotrienes $C_4$ and $D_4$ act as coronary and cerebral arterial vasoconstrictors, and these compounds may also have negative inotropic effects on the myocardium. In addition, the leukotrienes are important mediators of inflammatory disease through their ability to modulate leukocyte and lymphocyte function.

Many substituted di-tertiary-butylphenols are known. Generally, these compounds may be useful as antioxidants. Some of these compounds are also known to be active antiinflammatory agents. Compounds wherein 2,6-di-tertiary-butylphenol is substituted in the 4 position by an unsubstituted phenyl or certain simply-substituted phenyls are known as antiinflammatory agents. See, for example, U.S. Pat. No. 4,172,151 and references cited therein.

[No compounds wherein a 2,6-di-tertiary-butylphenol is substituted in the 4 position by an acylaminophenyl wherein such acylaminophenyl is substituted by a moiety which includes a carboxyl group are known.]

SUMMARY OF THE INVENTION

This invention relates to certain di-tertiary-butylphenols containing an acylaminophenyl group which in turn contains a carboxyl group. These compounds are useful as inhibitors of mammalian leukotriene biosynthesis. As such, these compounds are useful therapeutic agents for treating allergic conditions, asthma, cardiovascular disorders and inflammation. Pharmaceutical compositions comprising such compounds and pharmacological methods of using such compounds are also described.

DETAILED DESCRIPTION OF THE INVENTION

The present invention [relates to] *provides methods for inhibiting bronchoconstriction, methods for inhibiting leukotriene biosynthesis, and pharmaceutical compositions involving* compounds of Formula I:

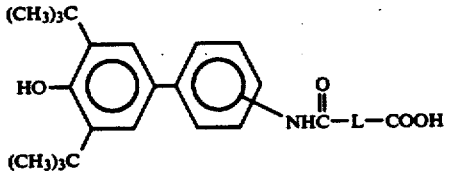

wherein L is divalent phenyl, straight-chain lower alkylene, the chain of which may optionally contain an ether or thioether linkage, or divalent cycloalkyl (preferably cyclohexyl), with the proviso that if L is divalent cycloalkyl with the amide carbonyl and the carboxyl in the 1,2 positions, then the amide carbonyl and the carboxyl are cis to each other; and carboxylate derivatives thereof selected from lower alkyl ester, (lower) alkylamino(lower)alkyl esters, pharmaceutically acceptable (lower)alkylamino (lower)alkyl ester acid-addition salts and pharmaceutically acceptable carboxylate salts.

The phrase "lower alkyl" as used in the instant specification and claims denotes straight or branched chain moieties containing one to about four carbon atoms. The phrase "cycloalkyl ring" denotes a hydrocarbon ring containing 5 or 6 carbon atoms therein. The phrase "lower alkylene" denotes moieties containing one to about four carbon atoms.

Presently preferred are *compositions and methods involving* compounds wherein the

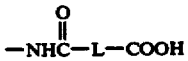

group is oriented para to the biphenyl bond.

*This invention also provides compounds of Formula I selected from the group consisting of N-(3',5'-di-tertiary-butyl-4'-hydroxy-2-biphenylyl)glutaramic acid, N-(3',5'-di-tertiary-butyl-4'-hydroxy-2-biphenylyl)diglycolamic acid, 2-{N-4-(3,5-di-t-butyl-4-hydroxyphenyl)-phenyl]carbamoyl}benzoic acid, cis-2-{N-[4-(3,5-di-t-butyl-4-hydroxyphenyl)phenyl]carbamyl}cyclohexanecarboxylic acid, and carboxylate derivatives thereof selected from lower alkyl esters, (lower) alkylamino(lower)alkyl esters, pharmaceutically acceptable (lower)alkylamino (lower)alkyl ester acid-addition salts and pharmaceutically acceptable carboxylate salts.*

It is well known to the art that pharmaceutically acceptable salts such as alkali metal, alkaline earth, aluminum and other metal and amine salts of pharmaceutically active carboxylic acids are the equivalents of the acids in terms of activity, and in some cases may even offer advantages in absorption, formulation and the like. Pharmaceutically-acceptable carboxylate salts of the compounds of [the invention] *Formula I* are prepared by reaction of the acid with a base and subsequent evaporation to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of [the invention] *Formula I* include alkyl esters and alkylamino esters and salts of the latter. In the ester derivatives, the hydrogen portion of the carboxylic acid group is replaced with an alkyl or substituted alkyl. The esters may be prepared by standard synthetic methods.

Compounds of Formula I may be prepared according to the method of Scheme 1 below wherein L is as defined above.

Scheme 1

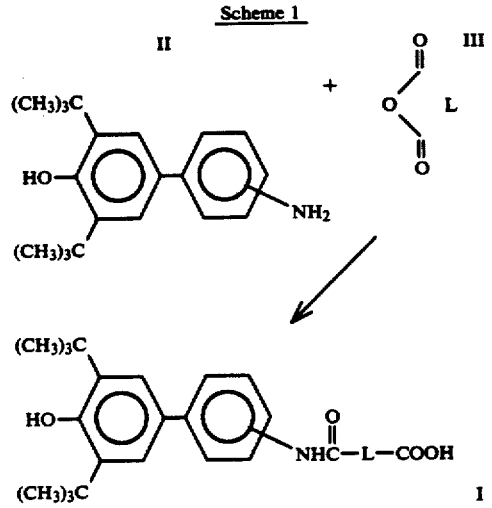

In Scheme 1, a diacid anhydride of Formula III is reacted with amino-3,5-di-tertiary-butyl-4-hydroxybiphenyl of Formula II. Suitable anhydrides of Formula III are known compounds such as glutaric anhydride, phthalic anhydride and the like. Compounds of Formula II are similarly known having been disclosed in, for example, U.S. Pat. No. 4,172,151. The reaction of Scheme 1 is carried out by combining the reactants in an inert solvent such as diethyl ether or glyme. The reaction mixture may optionally be heated. The products of Formula I are readily isolated using standard techniques, e.g., filtration, extraction and the like, and are purified by recrystallization.

Compounds of Formula I may also be prepared according to the method of Scheme 2 below wherein L is as defined above and Q is a carboxylate ester.

Scheme 2

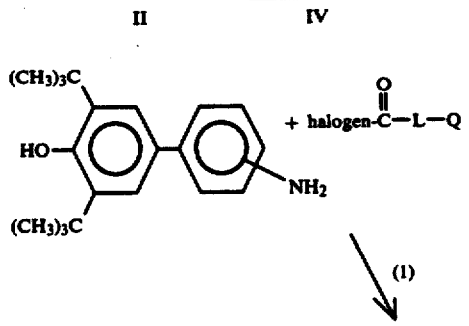

-continued

Scheme 2

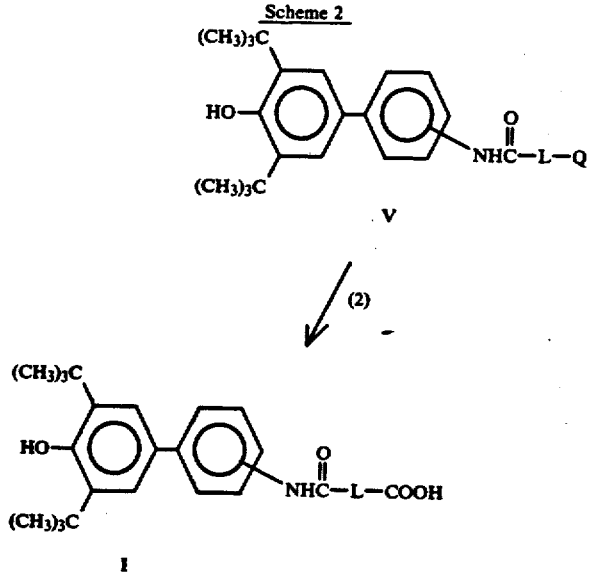

In Scheme 2, an acid halide of Formula IV is first reacted in Step (1) with an amino-3,5-di-tertiary-butyl-4-hydroxybiphenyl of Formula II. Suitable acid halides of Formula IV are known compounds such as methyl glutaryl chloride and the like. The reaction is carried out by combining the reactants in an inert solvent and the reaction mixture may optionally be heated. The compound of Formula V provided in Step (1) may then be readily converted to the acids of Formula I in Step 2 using conventional hydrolysis means.

The activity of compounds of Formula I may be demonstrated readily by in vivo testing. The in vivo test used may be any of those known to those skilled in the art. Preferably, bronchoconstriction in sensitized guinea pigs is measured upon antigen challenge. Active compounds are those which demonstrate an intraoeritoneal $ED_{40}$ of 100 mg per kg or less, and preferably an $ED_{40}$ of 50 mg per kg or less. Most preferred compounds are active at 25 mg per kg. This test is described in broad terms by Piechuta, et al., Immunology, 38, 385 (1979) and more specifically by Hammerbeck and Swingle, Int. Archs. Allergy Appl. Immun., 74, 84–90 (1984), both references being incorporated herein by reference. It was used in a modified form as follows: Male Hartley guinea pigs (250–600 g) were pretreated with an antihistamine, e.g., chlorpheniramine, then dosed intraperitoneally with a compound of the invention at a level of about 1 to 40 mg/kg 15 minutes prior to challenge or orally at the same dose 30 minutes prior to challenge. The animals were placed under an inverted dessicator jaw (18×14 cm) with a constant flow of air coming into the chamber from a compressed-air source to prevent hypoxia and were aerosol challenged with either water or ovalbumin at a concentration of 10 mg per ml. Air flow leaving the chamber and fluctuations due to respiration were monitored through a separate outlet with a Fleisch No. 0000 pneumotachograph (available from Beckman Instruments, Inc., Schiller Park, Ill.) coupled to a Beckman Type R dynograph (available from Beckman Instruments, Inc.). Aerosolization through a third outlet was made via a No. 4 DeVilbiss nebulizer (available from The DeVilbiss Company, Somerset, Pa.) for 90 seconds at 150 mm Hg. The characteristic respiratory patterns observed were summations of two air exchange processes occurring simultaneously in the chamber. One exchange process was due to inspiration and expiration of air into and out of the animal, while the other exchange process was due to the air flow into and out of the chamber due to respiratory movements. The tracing obtained was the mechanical representation of the summation of those flows. Superimposed on the tracings was a characteristic spiking ('notching'), which appears to be an exaggerated expiratory movement, the frequency of which correlates with the severity of the bronchoconstrictive reaction. The frequency of notching for 15-minute periods beginning 4 minutes after the beginning of the aerosol challenge was used for comparing various treatments. Effects were considered significant if the t value achieved $p<0.05$.

The compounds may also be treated in more specific tests for the inhibition of leukotriene synthesis. Active compounds are those which exhibit an $IC_{50}$ of 100 micromolar or less, and preferably less than 25 micromolar. Most preferred compounds exhibit an $IC_{50}$ of 10 micromolar or less. The compounds are tested in either intact cells or in cell sonicate. The intact cell assay is similar to that described by Verhagen et al., FEBS Letter 168, 23–28 (1984), incorporatd herein by reference. Human leukocytes are prepared using standard procedures. The cells are incubated in pH 7.4 Tris buffer containing 5 millimolar calcium chloride and 5 millimolar glutathione. After vehicle or drug incubation, the cells are activated with the calcium ionophore A 23187 (4 micrograms per ml). After 15 minutes at room temperature, the cells are centrifuged and the supernatants are stored for assay of $LTC_4$ content by radioimmunoassay. The cell sonicate assay utilizes the cell free leukotriene biosynthesis system of M. Steinhoff et al., Biochim. Biophy. Acta., 68, 28 (1980) incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhaus et al., FEBS Letter 146, 111–114, incorporated herein by reference. Drugs are dissolved in ethanol or dimethyl sulfoxide and preincubated for five minutes. Phenidone is used as a positive control.

The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release dosage forms. Dosage forms for administration by inhalation include aerosols and sprays and may be administered in metered dose.

For treating allergies or allergic reactions, the compound of Formula I may be administered by any conventional mode, e.g., orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area, salves, patches, controlled release patches, emulsions, etc. are convenient dosage forms.

For treating cardiovascular conditions, any suitable mode of administration, such as oral or intraperitoneal, may be used.

In addition to the common dosage forms listed above, the compounds of Formula I may also be administered for various utilities and indications or for inhibiting leukotriene synthesis by controlled release means and/or delivery devices.

In preparing suitable dosage forms, conventional compounding procedures and ingredients, e.g., diluents, carriers, etc. may be used. Examples of suitable solid carriers are lactose, terra alba, sucrose, talc, gelatin, agar, pectin, acacia, magnesium stearate, stearic acid and the like. Examples of suitable liquid carriers are syrup, peanut oil, olive oil, PEG-400, water and the like. Similarly, the carrier or diluent can include any time delay material well known to the art, such as glyceryl monostearate or glyceryl distearate, these being useful alone, or, for example, in combination with wax.

The following examples are provided to illustrate the invention, but are not intended to limit the invention.

EXAMPLE 1

Preparation of N-(3',5'-di-tertiary-butyl-4'-hydroxy-4-biphenylyl)-glutaramic Acid To a hot (70° C.) solution of 10.0 g (0.0336 mole) of the known compound 4'-amino-3,5-di-tertiary-butyl-4-hydroxybiphenyl in 100 ml of glyme was added 5.0 g (0.044 mole) of glutaric anhydride. After stirring for one hour, the mixture was cooled and poured into water. The precipitate was separated by filtration and recrystallized from a chloroform-hexane mixture to provide tan needles of N-(3',5'-di-tertiary-butyl-4'-hydroxy-4-biphenylyl)glutaramic acid, m.p. 217.5°-219° C. Analysis: Calculated for $C_{25}H_{33}NO_4$: % C, 73.0; % H, 8.1; % N, 3.4; Found: % C, 72.6; % H, 8.1; % N, 3.1.

EXAMPLE 2

Preparation of N-(3',5'-di-tertiary-butyl-4'-hydroxy-2-biphenylyl)-glutaramic Acid A solution of 1.9 g (6.4 mmole) of the known compound 2'-amino-3,5-di-tertiary-butyl-4-hydroxybiphenyl, 0.8 g (7.0 mmole) of glutaric anhydride and 50 ml of glyme was heated on a steam bath for three hours, then an additional 0.20 g of glutaric anhydride was added. The mixture was heated at reflux for six hours, then poured into water. The aqueous mixture was extracted with diethyl ether, and the ether extracts were then washed with 10% hydrochloric acid and water. The ether solution was extracted with dilute sodium carbonate solution, and the aqueous extracts were acidified to about pH 1 with 10% hydrochloric acid. An oil separated and crystallized after scratching to initiate crystal formation. Recrystallization of the residue from aqueous ethanol provided tan crystals of N-(3',5'-di-tertiary-butyl-4'-hydroxy-2-biphenylyl)glutaramic acid, m.p. 132°-134° C. Analysis: Calculated for $C_{25}H_{33}NO_4$: % C, 73.0; % H, 8.1; % N, 3.4; Found: % C, 73.0; % H, 8.0; % N, 3.3.

EXAMPLE 3

Preparation of N-(3',5'-di-tertiary-butyl-4'-hydroxy-4-biphenylyl)diglycolamic Acid To a mixture of 16.7 g (0.050 mole) of 4'-amino-3,-5-di-tertiary-butyl-4-hydroxybiphenyl hydrochloride and 7.0 g (0.060 mole) of oxydiacetic anhydride in 200 ml of glyme was added 0.050 mole of triethylamine and the solution was warmed at 70° C. for one hour. The solution was cooled and a 50:50 mixture of dichloromethane and water was added. The organic layer was separated, washed with water twice and dried over magnesium sulfate. Filtration and evaporation provided a residue which was triturated with hexane and chilled. The solid was separated by filtration. Recrystallization from a mixture of chloroform and hexane gave a grey solid. The solid was dissolved in 23 ml of ethanol, the solution was filtered and 10 ml of water was added to the filtrate. The filtrate was cooled and the resulting precipitate was separated by filtration and dried to provide N-(3',5'-di-tertiary-butyl-4'-hydroxy-4-biphenylyl)diglycolamic acid, m.p. 183°-184° C. Analysis: Calculated for $C_{24}H_{31}NO_5$: % C, 69.7; % H, 7.5; % N, 3.4; Found: % C, 69.9; % H, 7.6; % N, 3.1.

EXAMPLE 4

Preparation of 2-{N-[4-(3,5-di-t-butyl-4-hydroxyphenyl)-phenyl]carbamoyl}benzoic Acid To a solution of 2.97 g (0.01 mole) of 4'-amino-3,5-di-t-butyl-4-hydroxy biphenyl in 200 ml of diethyl ester was added a solution of 1.48 g (0.01 mole) of phthalic anhydride, and the resulting solution was stirred for about 16 hours. The solvents were removed under vacuum and the residual solid was recrystallized from a mixture of ethyl acetate and hexane to give 2.4 g of 2-{N-[4-(3,5-di-t-butyl-4-hydroxyphenyl)phenyl]carbamoyl}benzoic acid, m.p. 196°-198° C. Analysis: Calculated for $C_{28}H_{31}NO_4$: % C, 75.5; % H, 7.0; % N, 3.1; Found: % C, 75.5; % H, 7.1; % N, 3.0.

EXAMPLE 5

Preparation of cis-2-{N-[4-(3,5-di-t-butyl-4-hydroxyphenyl)phenyl]-carbamyl}cyclohexanecarboxylic Acid To a solution of 2.97 g of 4'-amino-3,5-di-t-butyl-4-hydroxybiphenyl in 200 ml of diethyl ether was added a solution of 1.54 g (0.01 mole) of cis-1,2-cyclohexanedicarboxylic anhydride in 75 ml of diethyl ether, and the resulting solution was stirred for about 16 hours. A solid was removed by filtration, rinsed with diethyl ether and hexane and then recrystallized from a mixture of ethyl acetate and hexane to give 3.17 g of solid cis-2-{N-[4-(3,5-di-t-butyl-4-hydroxyphenyl)phenyl]carbamyl}-cyclohexanecarboxylic acid, m.p. 217°-220° C. Analysis: Calculated for $C_{28}H_{37}NO_4$: % C, 74.5; % H, 8.3; % N, 3.1; Found: % C, 74.6; % H, 8.3; % N, 3.0.

What is claimed is:

[1. A compound of the formula

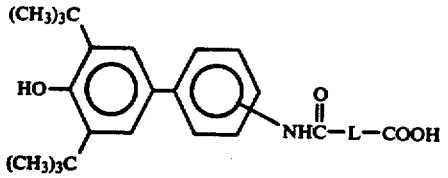

wherein L is divalent phenyl, straight-chained lower alkylene wherein the alkylene chain may optionally contain an ether or thioether linkage, or divalent cycloalkyl, with the proviso that when L is divalent cycloalkyl and the amide carbonyl and the carboxyl are on adjacent carbons, then the amide carbonyl and the carboxyl are cis to each other; or a carboxylate derivative thereof selected from a lower alkyl ester, a (lower)alkylamino(lower)alkyl ester, a pharmaceutically acceptable (lower)alkylamino(lower)alkyl ester acid addition salt and a pharmaceutically acceptable carboxylate salt.]

[2. A compound of claim 1 wherein the

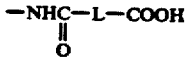

group is oriented para to the biphenyl bond.]

[3. A method for inhibiting bronchoconstriction due to an allergic reaction in a mammal comprising administering a compound according to claim 1 to said mammal in an amount effective to inhibit said constriction.]

[4. An antiallergic pharmaceutical composition comprising a compound according to claim 1 and a pharmaceutically acceptable carrier, said compound being present in an amount sufficient for providing an antiallergic response.]

[5. A method for inhibiting leukotriene biosynthesis in a mammal comprising administering a compound according to claim 1 to said mammal in an amount effective to inhibit said synthesis.]

*6. A method for inhibiting bronchoconstriction due to an allergic reaction in a mammal comprising administering to said mammal a compound of the formula*

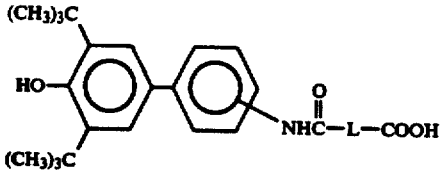

*wherein L is divalent phenyl, straight-chained lower alkylene wherein the alkylene chain may optionally contain an ether or thioether linkage, or divalent cycloalkyl, with the proviso that when L is divalent cycloalkyl and the amide carbonyl and the carboxyl are on adjacent carbons, then the amide carbonyl and the carboxyl are cis to each other; or a carboxylate derivative thereof selected from a lower alkyl ester, a (lower)alkylamino(lower)alkyl ester, a pharmaceutically acceptable (lower)alkylamino(lower)alkyl ester acid addition salt and a pharmaceutically acceptable carboxylate salt,*

*in an amount effective to inhibit said constriction.*

*7. A method for inhibiting leukotriene biosynthesis in a mammal comprising administering to said mammal a compound according of the formula*

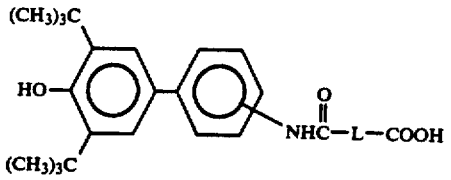

*wherein L is divalent phenyl, straight-chained lower alkylene wherein the alkylene chain may optionally contain an ether or thioether linkage, or divalent cycloalkyl, with the proviso that when L is divalent cycloalkyl and the amide carbonyl and the carboxyl are on adjacent carbons, then the amide carbonyl and the carboxyl are cis to each other; or a carboxylate derivative thereof selected from a lower alkyl ester, a (lower)alkylamino(lower)alkyl ester, a pharmaceutically acceptable (lower)alkylamino(lower)alkyl ester acid addition salt and a pharmaceutically acceptable carboxylate salt,*

*in an amount effective to inhibit said synthesis.*

*8. A compound selected from the group consisting of N-(3',5'-di-tertiary-butyl-4'-hydroxy-2-biphenylyl)-glutaramic acid, N-(3',5'-di-tertiary-butyl-4'-hydroxy-2-biphenylyl)diglycolamic acid, 2-{N-[4-(3,5-di-t-butyl-4-hydroxyphenyl)-phenyl]carbamoyl}benzoic acid, cis-2-{N-[4-(3,5-di-t-butyl-4-hydroxyphenyl)phenyl]carbamyl}cyclohexanecarboxylic acid, and a carboxylate derivative thereof selected from the group consisting of a lower alkyl ester, a (lower) alkylamino(lower)alkyl ester, a pharmaceutically acceptable (lower)alkylamino (lower)alkyl ester acid-addition salt and a pharmaceutically acceptable carboxylate salt.*

*9. A method for inhibiting bronchoconstriction due to an allergic response in a mammal, comprising administering to said mammal a compound according to claim 8 in an amount effective to inhibit said constriction.*

*10. An antiallergic pharmaceutical composition, comprising a compound according to claim 8 and a pharmaceutically acceptable carrier, said compound being present in an amount sufficient for providing an antiallergic response.*

*11. A method for inhibiting leukotriene biosynthesis in a mammal, comprising administering to said mammal a compound according to claim 8 in an amount effective to inhibit said synthesis.*

*12. An antiallergic pharmaceutical composition comprising a compound of the formula*

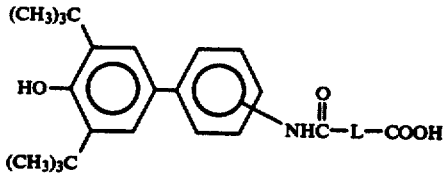

*wherein L is divalent phenyl, straight-chained lower alkylene wherein the alkylene chain may optionally contain an ether or thioether linkage, or divalent cycloalkyl, with the proviso that when L is divalent cycloalkyl and the amide carbonyl and the carboxyl are on adjacent carbons, then the amide carbonyl and the carboxyl are cis to each other; or a carboxylate derivative thereof selected from a lower alkyl ester, a (lower)alkylamino(lower)alkyl ester, a pharmaceutically acceptable (lower)alkylamino(lower)alkyl ester acid addition salt and a pharmaceutically acceptable carboxylate salt,*

*in a dosage form selected from the group consisting of a tablet, a capsule, an aerosol, a controlled release patch, and a powder, said compound being present in an amount sufficient for providing an antiallergic response.*

*13. An antiallergic pharmaceutical composition in a dosage form selected from the group consisting of a tablet, a capsule, an aerosol, a controlled release patch, and a powder, said dosage form comprising a compound according to claim 8, said compound being present in an amount sufficient for providing an antiallergic response.*

* * * * *

UNITED STATES PATENT AND TRADEMARK OFFICE

CERTIFICATE OF CORRECTION

PATENT NO. : Re. 33,574

DATED : April 23, 1991

INVENTOR(S) : Kirk et al.

It is certified that error appears in the above-identified patent and that said Letters Patent is hereby corrected as shown below:

| | |
|---|---|
| Col. 5, line 55 | "dessicator jaw" should read --dessicator jar-- |
| Col. 6, lines 25-26 | "(1984), incorporated hrein by reference. Human" should read --(1984). Human-- |
| Col. 6, lines 36-37 | "(1980) incorporated herein by reference, which consists" should read --(1980), which consists-- |
| Col. 6, lines 43-44 | "111-114, incorporated herein by reference. Drugs" should read --111-114. Drugs-- |

Signed and Sealed this

Nineteenth Day of January, 1993

*Attest:*

DOUGLAS B. COMER

*Attesting Officer*

*Acting Commissioner of Patents and Trademarks*